United States Patent [19]

Brophy et al.

[11] Patent Number: 5,336,826
[45] Date of Patent: Aug. 9, 1994

[54] OXIDATION OF METHANE OVER HETEROGENEOUS CATALYSTS

[75] Inventors: John H. Brophy, Camberley; Steven R. Wade, Chertsey, both of England

[73] Assignee: The British Petroleum Company p.l.c., London, England

[21] Appl. No.: 944,939

[22] Filed: Dec. 22, 1986

[30] Foreign Application Priority Data

Jan. 7, 1986 [GB] United Kingdom ............... 8600260

[51] Int. Cl.⁵ .............................. C07C 2/00
[52] U.S. Cl. .................... 585/500; 585/700; 585/541; 585/654; 585/658; 585/661; 585/943
[58] Field of Search ............... 585/500, 700, 943, 541, 585/654, 658, 661

[56] References Cited

U.S. PATENT DOCUMENTS

| | | | |
|---|---|---|---|
| 4,450,313 | 5/1984 | Eastman | 585/661 X |
| 4,476,344 | 10/1984 | Kimble | 585/661 |
| 4,523,049 | 6/1985 | Jones et al. | 585/500 |
| 4,650,781 | 3/1987 | Jones et al. | 585/500 |
| 4,658,077 | 4/1987 | Kolts | 585/500 X |

FOREIGN PATENT DOCUMENTS

| | | |
|---|---|---|
| 34197 | 5/1985 | Australia . |
| 42905 | 11/1985 | Australia . |
| 57548 | 12/1986 | Australia . |
| 57883 | 1/1987 | Australia . |
| 57885 | 2/1987 | Australia . |
| 0189079 | 7/1986 | European Pat. Off. ............ 585/700 |
| WO04821 | 11/1985 | PCT Int'l Appl. . |

*Primary Examiner*—Helen M. S. Sneed
*Assistant Examiner*—E. D. Irzinski
*Attorney, Agent, or Firm*—Brooks Haidt Haffner & Delahunty

[57] ABSTRACT

Higher hydrocarbons are produced from methane by reacting the methane at elevated temperature, suitably in the range from 600° to 800° C., with an oxygen-containing gas having a ratio of methane to oxygen of greater than the stoichiometric ratio for complete combustion in the presence as catalyst of a lithium-doped material which under the reaction conditions is a physically base-stable, non-melting, oxygen-stable compound of an element of Groups III to VIII of the Periodic Table of the Elements including the rare earth elements.

10 Claims, No Drawings

OXIDATION OF METHANE OVER HETEROGENEOUS CATALYSTS

The present invention relates in general to a process for the conversion of methane to higher hydrocarbons and in particular to a process for partially oxidising methane to $C_2$ and higher hydrocarbons over heterogeneous oxidation catalysts.

The conversion of methane to higher hydrocarbon products over reducible oxide catalysts has been extensively studied in the recent past. Representative of the art describing such a process may be mentioned for example U.S. Pat. Nos. 4,443,644; 4,443,645; 4,443,646; 4,443,647; 4,443,649; 4,495,374; 4,499,322; 4,443,648; 4,444,984; 4,547,611; 4,523,049; 4,544,785; 4,499,323; 4,544,784; 4,523,050; 4,547,607; 4,499,324; 4,547,608; 4,544,786; 4,517,398 and 4,547,610.

U.S. Pat. No. 4,482,646 describes an oxidative dehydrogenation process for a paraffin or a mixture of paraffins having from 2 to 5 carbon atoms employing a catalyst composition comprising lithium and titanium.

In Nature, vol 314, 25.4.85, pages 721/722, Ito and Lunsford report that lithium-doped magnesium oxide (Li/MgO) in the presence of oxygen has a high activity for abstracting H from $CH_4$ to form $.CH_3$ radicals which thereafter couple to form $C_2H_6$ and $C_2H_4$ in high yields under conventional catalytic conditions. The $.CH_3$ radicals are believed to be formed at ($Li^+O^-$) centres on MgO which has previously been observed in Li-doped MgO single crystals.

We have now found that, contrary to the postulated mechanism, a wide variety of metal oxides can be used in place of MgO.

Accordingly, the present invention provides a process for the production of higher hydrocarbons from methane which process comprises reacting methane at elevated temperature with an oxygen-containing gas having a ratio of methane to oxygen of greater than the stoichiometric ratio for complete combustion in the presence as catalyst of a lithium-doped material which under the reaction conditions is a physically base-stable, non-melting, oxygen-stable compound of an element of Groups III to VIII of the Periodic Table of the Elements including the rare earth elements.

The Periodic Table of the Elements as used throughout this specification is the Periodic Table of the Elements as found in Advanced Inorganic Chemistry by F. A. Cotton and G- Wilkinson, 2nd Edition, Interscience, 1966.

The catalyst is a lithium-doped material. Lithium may be provided in a number of forms, including the halide, for example the chloride, the carbonate, the bicarbonate, the sulphate and the nitrate, preferably as the the carbonate. The material to be doped with lithium must fulfill a number of criteria, it must under the reaction conditions (i) be physically stable to bases, (ii) be non-melting and (iii) be oxygen stable. Generally, the oxides of metals of Groups III to VIII of the Periodic Table including metals of the lanthanide and actinide series will be found suitable. Materials which fulfill the aforesaid criteria include, but are no means restricted to, alumina, niobia, titania, zirconia, ceria, thoria, tantala and boria. Ceria, for example, may be used in the commercially available form comprising a mixture of rare earth metal oxides of which the major constituent is ceria.

The precise nature of the catalyst under the conditions of the reaction is not known with any degree of certainty. It is believed to comprise, after oxidative activation, principally lithium carbonate and a metal oxide, though the metal oxide may be converted into a lithium compound, for example a titanate, aluminate, zirconate or borate.

Lithium may be present in an amount up to about 18% w/w, but amounts in the range from 1 to 10% w/w will usually be found suitable. The catalyst may suitably be prepared by any of the techniques conventionally employed for catalyst preparation, for example by impregnation, precipitation or coprecipitation.

It has been found that the material of the partial oxidation reactor has a significant effect upon the nature of the products obtained. Whereas stainless steels produce a considerable proportion of carbon oxides, quartz tends to produce $C_2$ hydrocarbons. For this reason it is preferred to use a reactor the walls of which have either been passivated by suitable chemical treatment or provided with a glass lining. The reactor may be of the fixed bed or fluid bed type, if necessary with means provided for the removal of heat.

Before use in the process of the invention the catalyst is preferably activated, suitably by heating at elevated temperature in the presence of an oxygen-containing gas.

The methane may be substantially pure or may be mixed with other gaseous paraffinic hydrocarbons, for example ethane and/or propane. Inert diluents, for example argon, helium or nitrogen, may also be employed if desired.

The oxygen-containing gas may be, for example, air or an air/oxygen mixture. Substantially pure oxygen may also be used as the oxygen-containing gas.

A suitable composition of the methane/oxygen-containing gas mixture at atmospheric pressure is a molar ratio of methane to oxygen of from 1.1 to 50 times the stoichiometric ratio of methane/oxygen for complete combustion to carbon dioxide and water. These limits are extendable if operation at pressures greater than atmospheric are envisaged or if the feed gases are preheated. It is preferred to operate at high methane to oxygen ratios within the aforesaid range because higher selectivities to $C_2$ hydrocarbons are obtained, though methane conversions are generally lower. Preferably, conditions are chosen which maximize the selectivity to $C_2$ hydrocarbons and the methane conversion.

The process may suitably be operated at a temperature in the range from 600° to 800° C., preferably from 650° to 750° C. The pressure may suitably be atmospheric pressure, though elevated pressures may be employed.

The methane and/or the oxygen-containing gas may suitably be preheated, if required, prior to contact with the catalyst.

The invention will now be further illustrated by reference to the following Examples.

Catalyst Preparation

Catalysts were prepared by dry mixing AR grade lithium carbonate and the appropriate metal oxide with a mechanical stirrer. Sufficient water was added to form a smooth thick slurry which was mixed for a further ten minutes. The resulting slurry was dried in air at 125° C., and then calcined in air at 800° C. for six hours. The product was crushed and sieved to 1.18 to 0.6 mm.

EXAMPLES 1 TO 25

The catalyst was charged into a quartz reactor mounted in a vertical tubular furnace, and heated to the respective temperature in a stream of nitrogen. The nitrogen stream was then replaced with a mixed methane/oxygen feed, and after steady state had been achieved (approx 30 mins), the products were analysed by gas chromatography.

The following catalysts were employed.

Example 1—$TiO_2/Li_2CO_3$, Li:Ti atomic ratio=2.0.

Examples 2 and 3—$TiO/Li_2CO_3$, Li:Tt atomic ratio=2.0.

Examples 4 to 8—$CeO_2/Li_2CO_3$, Li:Ce atomic ratio=2.0.

Examples 9 to 12—$ZrO_2/Li_2CO_3$, Li:Zr atomic ratio=2.0.

Examples 13 to 16—Rare earth metal oxide/$Li_2CO_3$, the rare earth metal oxide being a commercially available rare earth metal oxide mixture, principally comprising ceria, Li:rare earth metal atomic ratio=2.0.

Example 17—$LiAlO_2$, Li:Al atomic ration=1.0.

Example 18—$Li_2CO_3/K_2CO_3/LiAlO_2$, Li:K:Al atomic ratios=1:0.1:0.83

Examples 19 and 20—$Li_2CO_3/ThO_2$, Li:Th atomic ratio=1.9

Example 21—$Li/Pr_6O_{11}$, Li:Pr atomic ratio=1:5.4

Examples 22 and 23—$Na_2CO_3/Li_2CO_3/Pr_6O_{11}$, Li:Na:Pr atomic ratio=1:1:6.6.

The reaction conditions and the product analyses are given in Tables 1 to 3.

TABLE 1

| Example | Catalyst | $CH_4:O_2$ ratio (nominal) | Max Bed Temp (°C.) | GHSV ($h^{-1}$) | Conversions (%) $CH_4$ | $O_2$ | Carbon Selectivities (%) $C_2H_4$ | $C_2H_6$ | $C_3+$ | CO | $CO_2$ |
|---|---|---|---|---|---|---|---|---|---|---|---|
| 1 | $TiO_2/Li_2CO_3$ | 2:1 | 778 | 600 | 36.8 | 98.5 | 31.1 | 9.2 | 2.3 | 9.0 | 48.5 |
| 2 | $TiO/Li_2CO_3$ | 2:1 | 775 | 600 | 35.3 | 98.4 | 30.6 | 7.4 | 4.1 | 7.3 | 50.7 |
| 3 | $TiO/Li_2CO_3$ | 4:1 | 760 | 600 | 21.9 | 97.8 | 41.5 | 13.1 | 3.4 | 0 | 42.0 |
| 4 | $CeO_2/Li_2CO_3$ | 2:1 | 760 | 600 | 37.6 | 99.8 | 30.9 | 14.0 | 6.3 | 0 | 48.8 |
| 5 | $CeO_2/Li_2CO_3$ | 2:1 | 788 | 600 | 37.6 | 99.8 | 33.9 | 13.9 | 4.5 | 0 | 47.7 |
| 6 | $CeO_2/Li_2CO_3$ | 2:1 | 692 | 600 | 36.0 | 98.4 | 30.8 | 14.1 | 5.0 | 0 | 50.0 |
| 7 | $CeO_2/Li_2CO_3$ | 4:1 | 744 | 600 | 25.7 | 99.7 | 35.5 | 21.0 | 7.3 | 0 | 36.1 |
| 8 | $CeO_2/Li_2CO_3$ | 4:1 | 771 | 600 | 26.2 | 99.8 | 38.7 | 18.8 | 5.3 | 0 | 37.2 |

TABLE 2

| Example | Catalyst | $CH_4:O_2$ ratio (nominal) | Max Bed Temp (°C.) | GHSV ($h^{-1}$) | Conversions (%) $CH_4$ | $O_2$ | Carbon Selectivities (%) $C_2H_4$ | $C_2H_6$ | $C_3+$ | CO | $CO_2$ |
|---|---|---|---|---|---|---|---|---|---|---|---|
| 9 | $ZrO_2/Li_2CO_3$ | 2:1 | 787 | 600 | 40.6 | 99.8 | 30.4 | 11.3 | 3.7 | 0 | 54.6 |
| 10 | $ZrO_2/Li_2CO_3$ | 2:1 | 794 | 600 | 37.9 | 99.8 | 32.3 | 13.2 | 3.7 | 0 | 50.9 |
| 11 | $ZrO_2/Li_2CO_3$ | 4:1 | 777 | 600 | 27.3 | 99.6 | 38.0 | 18.8 | 4.8 | 0 | 38.3 |
| 12 | $ZrO_2/Li_2CO_3$ | 4:1 | 751 | 600 | 26.2 | 99.4 | 34.9 | 20.9 | 4.8 | 0 | 39.5 |
| 13 | $REO_x*/Li_2CO_3$ | 2:1 | 725 | 600 | 36.0 | 96.7 | 28.8 | 10.8 | 3.0 | 15.6 | 41.8 |
| 14 | $REO_x*/Li_2CO_3$ | 2:1 | 762 | 600 | 33.0 | 98.1 | 34.2 | 11.6 | 5.4 | 0 | 48.8 |
| 15 | $REO_x*/Li_2CO_3$ | 2:1 | 789 | 600 | 33.4 | 99.2 | 36.4 | 11.5 | 4.7 | 0 | 47.5 |
| 16 | $REO_x*/Li_2CO_3$ | 2:1 | 836 | 1200 | 32.2 | 98.8 | 28.4 | 11.5 | 3.0 | 0 | 57.1 |

Notes:
a = Ratios for rare earth oxides calculated as pure $CeO_2$
$REO_x$ = commercial mixture of rare earth metal oxides

TABLE 3

| Example | Catalyst | $CH_4:O_2$ ratio (nominal) | Max Bed Temp (°C.) | GHSV ($h^{-1}$) | Conversions (%) $CH_4$ | $O_2$ | Carbon Selectivities (%) $C_2H_4$ | $C_2H_6$ | $C_3+$ | CO | $CO_2$ | $C_2+$ |
|---|---|---|---|---|---|---|---|---|---|---|---|---|
| 17 | $LiAlO_2$ | 2:1 | 791 | 600 | 38.9 | 99.6 | 28.8 | 8.3 | 6.3 | 0 | 56.6 | 43.4 |
| 18 | $Li_2CO_3/K_2CO_3/LiAlO_2$ | 2:1 | 792 | 600 | 33.0 | 99.7 | 28.5 | 14.1 | 5.3 | 0.4 | 51.8 | 47.9 |
| 19 | $Li_2CO_3/ThO_2$ | 2:1 | 805 | 600 | 31.4 | 99.7 | 33.4 | 12.5 | 7.3 | 0 | 46.8 | 53.2 |
| 20 | $Li_2CO_3/ThO_2$ | 12:1 | 749 | 600 | 8.2 | 97.8 | 32.8 | 36.9 | 6.1 | 0 | 24.2 | 75.8 |
| 21 | $Li/Pr_6O_{11}$ | 2:1 | 784 | 600 | 40.1 | 99.8 | 28.3 | 16.3 | 7.9 | 0 | 47.5 | 52.5 |
| 22 | $Li_2CO_3/Na_2CO_3/Pr_6O_{11}$ | 2:1 | 758 | 600 | 41.2 | 99.7 | 30.4 | 14.8 | 7.6 | 0 | 47.1 | 52.9 |
| 23 | $Li_2CO_3/Na_2CO_3/Pr_6O_{11}$ | 8:1 | 722 | 600 | 15.3 | 100 | 30.3 | 37.4 | 9.9 | 0.2 | 22.3 | 77.5 |

We claim:

1. A process for the production of higher hydrocarbons from methane which comprises reacting methane in a temperature range of about 600° to 800° C. with an oxygen-containing gas having a ratio of methane to oxygen of greater than the stoichiometric ratio for complete combustion in the presence of a lithium-doped material as catalyst under reaction conditions sufficient to convert said methane to said higher hydrocarbons, said catalyst consisting essentially of:
   (i) a compound selected from the group consisting of niobia, zirconia, thoria, tantala and boria; and
   (ii) a lithium-dopant.

2. A process according to claim 1 wherein the lithium is added to the material to be doped in the form of either a halide, the carbonate, the bicarbonate, the sulphate or the nitrate.

3. A process according to claim 1 wherein lithium is present in said catalyst in an amount up to 18% by weight.

4. A process according to claim 1 wherein lithium is present in said catalyst in an amount from 1 to 10% by weight.

5. A process according to claim 1 wherein prior to reaction the catalyst is activated by heating said catalyst in the presence of an oxygen-containing gas.

6. A process according to claim 1 wherein the molar ratio of methane to oxygen in the methane/oxygen-containing gas mixture at atmospheric pressure is from 1.1 to 50 times the stoichiometric ratio of methane to oxygen for complete combustion to carbon dioxide and water.

7. A process according to claim 1 wherein the temperature range is from about 650° to 750° C.

8. A process according to claim 5 wherein said catalyst is heated to about 800° C.

9. A process according to claim 6 wherein said ratio of methane to oxygen is in the range of about 1.1 to 4 times the stoichiometric ratio of methane to oxygen for complete combustion to carbon dioxide and water.

10. A process according to claim 9, wherein said range is about 2 to 4.

* * * * *

UNITED STATES PATENT AND TRADEMARK OFFICE
CERTIFICATE OF CORRECTION

PATENT NO. : 5,336,826
DATED : August 9, 1994
INVENTOR(S) : John H. Brophy, et. al.

It is certified that error appears in the above-indentified patent and that said Letters Patent is hereby corrected as shown below:

Title page, col. 2, under Abstract:  10 Claims should read-- 11 Claims--.

Add the following claim:

11.  A process as defined in claim 1 wherein said lithium dopant is lithium carbonate, the lithium is present in the catalyst in an amount of in the range of from 1 to 10% by weight, the molar ratio of methane to oxygen containing gas mixture of atmospheric pressure is from 1.1 to 50 times the stoichiometric ratio of methane to oxygen for complete combustion to carbon dioxide and water, and the temperature is in the range of from about 600 to 800°C.

Signed and Sealed this

Thirteenth Day of December, 1994

Attest:

BRUCE LEHMAN

*Attesting Officer*    *Commissioner of Patents and Trademarks*